(12) United States Patent
Veruva et al.

(10) Patent No.: US 12,102,722 B2
(45) Date of Patent: Oct. 1, 2024

(54) NAPPED COATED WOUND DRESSING

(71) Applicant: Ethicon, Inc., Somerville, NJ (US)

(72) Inventors: Sai Veruva, Somerville, NJ (US);
Jianguo Zhou, Somerville, NJ (US);
Joseph Vliet, Somerville, NJ (US);
Gerard Llanos, Somerville, NJ (US)

(73) Assignee: Ethicon, Inc., Raritan, NJ (US)

( * ) Notice: Subject to any disclaimer, the term of this patent is extended or adjusted under 35 U.S.C. 154(b) by 287 days.

(21) Appl. No.: 16/895,150

(22) Filed: Jun. 8, 2020

(65) Prior Publication Data
US 2021/0379237 A1   Dec. 9, 2021

(51) Int. Cl.
| | | |
|---|---|---|
| *A61L 15/22* | (2006.01) | |
| *A61F 13/00* | (2024.01) | |
| *A61F 13/15* | (2006.01) | |
| *A61L 15/32* | (2006.01) | |
| *A61L 15/42* | (2006.01) | |
| *A61L 15/44* | (2006.01) | |
| *A61L 15/64* | (2006.01) | |
| *B29C 48/00* | (2019.01) | |
| *B29L 31/00* | (2006.01) | |

(52) U.S. Cl.
CPC ...... *A61L 15/225* (2013.01); *A61F 13/00063* (2013.01); *A61L 15/32* (2013.01); *A61L 15/425* (2013.01); *A61L 15/44* (2013.01); *A61L 15/64* (2013.01); *A61F 2013/00676* (2013.01); *A61F 2013/00863* (2013.01); *A61F 2013/15967* (2013.01); *A61L 2300/254* (2013.01); *A61L 2300/43* (2013.01); *A61L 2400/04* (2013.01); *B29C 48/0018* (2019.02); *B29K 2995/006* (2013.01); *B29L 2031/753* (2013.01)

(58) Field of Classification Search
None
See application file for complete search history.

(56) References Cited

U.S. PATENT DOCUMENTS

| | | | |
|---|---|---|---|
| 3,526,224 | A | 9/1970 | Potts |
| 5,062,418 | A | 11/1991 | Dyer |
| (Continued) | | | |

FOREIGN PATENT DOCUMENTS

| | | | |
|---|---|---|---|
| CN | 1293025 A | 5/2001 | |
| CN | 1625625 A | 6/2005 | |
| (Continued) | | | |

OTHER PUBLICATIONS

Simoes et al. "Biofunctionalization of electrospun poly(caprolactone) fibers with Millard reaction products for wound dressing application", Reactive and Functional Polymers, 131, 191-202 (Year: 2018).*

(Continued)

*Primary Examiner* — Isis A Ghali
(74) *Attorney, Agent, or Firm* — David R. Crichton; Leo B. Kriksunov

(57) ABSTRACT

The present invention is directed to an absorbable hemostatic patch that utilizes a biocompatible fibrous, fabric substrate that is melt-blown and napped or loosened at the surface, with the substrate having a low-profile, high flexibility, strength and porosity that is suitable for coating cross-linkable active molecules and ultimately effective for use as a hemostat in situations of problematic bleeding.

9 Claims, 4 Drawing Sheets

(56) References Cited

U.S. PATENT DOCUMENTS

| | | | |
|---|---|---|---|
| 5,607,798 A * | 3/1997 | Kobylivker | C08L 23/12 604/382 |
| 6,152,943 A | 11/2000 | Sawhney | |
| 6,165,201 A | 12/2000 | Sawhney et al. | |
| 6,179,862 B1 | 1/2001 | Sawhney | |
| 6,514,534 B1 | 2/2003 | Sawhney | |
| 6,566,406 B1 | 5/2003 | Pathak | |
| 6,605,294 B2 | 8/2003 | Sawhney | |
| 6,673,093 B1 | 1/2004 | Sawhney | |
| 6,703,047 B2 | 3/2004 | Sawhney et al. | |
| 6,790,798 B1 | 9/2004 | Suzuki et al. | |
| 6,818,018 B1 | 11/2004 | Sawhney | |
| 6,942,896 B1 | 9/2005 | Martin | |
| 7,009,034 B2 | 3/2006 | Pathak et al. | |
| 7,347,850 B2 | 3/2008 | Sawhney | |
| 8,287,909 B2 | 10/2012 | Martin et al. | |
| 2002/0106409 A1 * | 8/2002 | Sawhney | A61K 47/34 424/484 |
| 2006/0167180 A1 * | 7/2006 | Plaut | C08F 290/12 525/187 |
| 2009/0246238 A1 | 10/2009 | Gorman et al. | |
| 2011/0070288 A1 | 1/2011 | Curtis et al. | |
| 2011/0045047 A1 | 2/2011 | Bennett | |
| 2011/0280919 A1 | 2/2011 | Higgins et al. | |
| 2013/0084323 A1 * | 4/2013 | Riebman | A61P 7/04 530/356 |
| 2013/0096063 A1 | 4/2013 | Hedrich et al. | |
| 2014/0073705 A1 | 3/2014 | Kelly et al. | |
| 2014/0178446 A1 | 6/2014 | Zhu et al. | |
| 2015/0223928 A1 | 8/2015 | Limem et al. | |
| 2015/0351776 A1 | 12/2015 | Swayze et al. | |
| 2017/0233913 A1 | 8/2017 | Shimada et al. | |

FOREIGN PATENT DOCUMENTS

| | | |
|---|---|---|
| EP | 2331854 A1 | 6/2011 |
| EP | 2529044 A2 | 12/2012 |
| EP | 3255188 A1 | 12/2017 |
| WO | 2007117385 A1 | 10/2007 |
| WO | 2011037760 A2 | 3/2011 |
| WO | 2011146359 A1 | 11/2011 |
| WO | 2013113906 A1 | 8/2013 |
| WO | 2015092797 A1 | 6/2015 |
| WO | 2017074671 A1 | 5/2017 |

OTHER PUBLICATIONS

Gupta (Textile-based smart wound dressings), Indian Journal of Fibre & Textile Research; vol. 35, pp. 174-187, Jun. 2010.*
International Search Report dated Sep. 3, 2021 for International Application No. PCT/IB2021/054986.

* cited by examiner

NAPPED COATED WOUND DRESSING

BACKGROUND

Absorbable hemostatic patches containing two cross-linkable components have been described in the literature including in US Publication No. 2011/0045047 A1. The cross-linkable components for such patches can be a pair of co-reactive compounds or a substrate coated with a co-reactive compound having available units that can form covalent cross-links with the corresponding co-reactive group on the substrate. Plasma derived biologic components that initiate, enhance and/or support the hemostatic cascade to generation of fibrin clots have also been applied onto substrates of various construction and materials.

SUMMARY OF THE INVENTION

The present invention relates to an absorbable hemostatic patch for sealing, and more particularly, to an economically-viable elastic-layered nonwoven matrix substrate, comprised of melt-blown microfibers, that is napped or loosened at the surface for high tissue adhesion. The napped substrate has uniquely high surface area and suitability for coating cross-linkable active molecules (e.g. PEGs) in the development of a highly functional low-profile hemostatic patch, that would otherwise lack good tissue adhesion properties.

The present invention is directed to an absorbable hemostatic nonwoven patch and wound dressing that utilizes a biocompatible fibrous, fabric substrate that is melt-blown and napped or loosened at the surface; with the substrate having a low-profile, high flexibility, strength and porosity that is suitable for coating cross-linkable active molecules and ultimately effective for use as a hemostat in situations of problematic bleeding.

DETAILED DESCRIPTION

Figure 1:
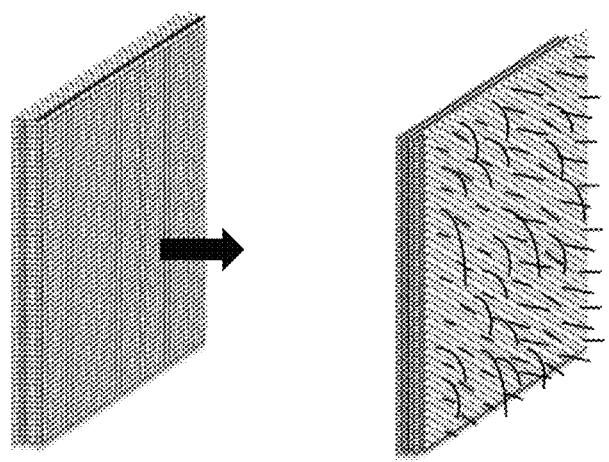
FIG. 1 is a schematic, exploded diagram of the standalone melt-blown patch whose surface fibers are raised, and matrix loft increased by napping methods.

The present invention is directed to a matrix that is particularly suited for coating as the napped surface has increased surface area for coating individual melt-blown fibers in the nonwoven matrix. A preferred high matrix loft is produced via a process of napping that loosens tightly entangled fibers, increasing matrix loft and overall volume that enables greater penetration depth for a subsequently applied coating layer.

One of the benefits of the present invention is the resulting wound dressing has sidedness since the surface that has been napped can be easily identified as the napped and coated face that should be applied onto a tissue surface.

The inventive wound dressing exhibits strong patch adhesion to tissue as the napped surface results in both higher amount of coated fibers and greater surface roughness, that together enhance adhesion at the patch-tissue interface.

Another advantage of the present invention is a low-profile patch that is easy to handle, with relatively low thickness and density that do not compromise functionality when napped, and can be easily be handled in smaller spaces. Patch may also need reduced compression time to seal.

Another advantage of the present invention is that the degree of napping can be modulated to allow for specific characteristics, e.g. decreasing stiffness with increasing degree of napping.

The present inventive wound dressing exhibits high tissue conformability as the combination of elastic-layered and roughened matrix allows for high compliance with the tissue if the tissue expands or moves.

In one embodiment, the present invention can be produced having tailored absorption time/biocompatibility as the melt-blown nonwoven matrix can be fabricated using biocompatible and absorbable materials by, for example, pre-irradiation and/or modulating fiber diameter and polymer structure during melt extrusion and crystallization respectively.

In one embodiment, a nonwoven base substrate is generated from an absorbable and biocompatible polyester material, such as Monocryl®, a copolymer of glycolide and epsilon-caprolactone, by extrusion through a linear die containing several hundred small orifices. Convergent streams of hot air attenuate the molten polymer to form extremely fine-diameter fibers. High-velocity air blows the fibers onto a collecting drum, forming one sheet of the melt-blown non-woven fabric. Process factors, such as drum speed and distance between the drum and surface of die, are selected to obtain preferred fiber diameter and orientation of fibers on formed web, which in-turn govern the resulting fiber diameter, pore-size and density of the nonwoven matrix.

The drum size, while dependent on the length of the polymer-extrusion die, is arbitrary and can be scaled up for large-scale manufacture of melt-blown sheets. The drum speed is inversely proportional to the non-woven matrix density per unit-area, and is inherently associated with fiber diameter, specific surface area and the overall porosity in the layer. The collector distance also affects matrix characteristics as increasing the gap between the polymer-extrusion die and the drum better randomizes fiber thickness and orientation.

The present invention identified preferred drum speeds in the range of 0.08-0.41 m/s, more preferably 0.12-0.37 m/s, most preferably 0.15-0.2 m/s, and distances in the range of 10 to 40 inches, more preferably in the range of 15-35, most preferably in the range of 20-30 in order to tailor and generate nonwoven membranes that were microporous, water-impermeable and low-profile (thickness).

The ranges were established using Monocryl® for which the material properties (e.g. 1.67 intrinsic viscosity) may affect fiber characteristics to a small degree, that in-turn play into porosity, density and stiffness of the overall matrix. However, the ranges should showcase the same trends irrespective of material specifics (for example, increasing the drum speed will reduce patch density for both Monocryl® and Vicryl®, a Polyglactin 910, a polyglycolic acid, and at the very least, the ranges we determined are viable starting points). Biodegradable polymers of interest that can be melt-blown include and are not limited to polyglycolic acid (PGA), poly(lactic-co-glycolic acid) (PLGA), polylactic acid (PLA), polydioxanone (PDS) and caprolactone/glycolide polyesters, such as poly(caprolactone-co-glycolide).

The present invention, prior to napping, identified preferred thickness in the range of 0.30-1.5 mm, more preferably 0.6-0.95 mm, most preferably 0.85-0.90 mm. While this starting thickness can vary, post-napping, the present invention identified the preferred increase in matrix height in the range of approximately 50-250% the original thickness, more preferably 55-175%, most preferably 125-165%.

The present invention, identified preferred density in the range of 140-250 mg/cm$^3$, more preferably 140-200 mg/cm$^3$, most preferably 140-150 mg/cm$^3$. The densities are not expected to change notably post-napping.

The present invention identified a preferred pore size distribution, based on micro-CT analysis, in the range of 0.01-0.5 mm, with majority of the pores in the range of 0.1-0.3 mm. Additionally from the micro-CT analysis, the invention identified the total open porosity of the matrix to be approximately 85%.

Meltblowing these polymers provides a unique advantage in generating ultra-fine fibers. The present invention of the melt-blown nonwoven identified fine fibers and a diameter in the in the range of 1-250 micrometers, preferably in the range of 1-90 microns.

In one embodiment, prior to napping, a standalone melt-blown patch is generated by extruding another sheet of melt-blown polyester-based nonwoven onto the collecting drum before crystallization of the former sheet. A plurality of discrete sheets are deposited onto the drum to create a multi-layered matrix. Then, the surface is modified to increase surface area for coatings and sidedness by napping. The napping effects are achieved by using abrasive techniques to mechanically raise the ends of fibers on the surface of the patch and simultaneously also increase the matrix loft as entanglements of fibers below the surface are loosened from the process.

Current napping methods employ both manual and automatic tools. For manual napping, a steel file card (e.g. 3.75") is used to brush the surface of the nonwoven fabric unidirectionally several times until fibers begin to dislodge from the surface (5-15 times is preferred working range for this method). For automatic napping, a bench-top drill press is used with a crimped wire wheel (e.g. 0.25" stem, 3" diameter) attachment. Other instruments such as glass, wire brushes and abrasive flap wheels can also be utilized the achieve different degrees of napping. Additionally, high-pressure air, vacuum or water-jets can also be utilized to loosen the matrix. In order to achieve extensive napping without destructive abrasion, matrices can be subjected to heat to soften the fibers prior to brushing. The napping increases cross-sectional and specific surface area for coating cross-linkable active molecules (FIG. 1) that ultimately provides potential for superior structural integration of the hemostatic patch with tissue for enhanced adhesion.

The degree of napping can be characterized by measurement of the increased cross-sectional height and area per density that results from the process. The most preferred process of moderately napping the surface raises the average fiber to provide a 161% increase in matrix height (FIG. 2; Table 1).

TABLE 1

Increase in matrix height from napping

| Condition | Density (mg/cm$^2$) | Matrix Height Δ (%) |
|---|---|---|
| Substrate A; No napping | 13.6 | — |
| Substrate A; Mildly Napped | 13.2 | 54.70 |

TABLE 1-continued

Increase in matrix height from napping

| Condition | Density (mg/cm$^2$) | Matrix Height Δ (%) |
|---|---|---|
| Substrate B; No napping | 13.3 | — |
| Substrate B; Moderately Napped | 13.3 | 161.11 |
| Substrate C; No napping | 12.9 | — |
| Substrate C; Highly Napped | 12.8 | 252.81 |

Figure 2:
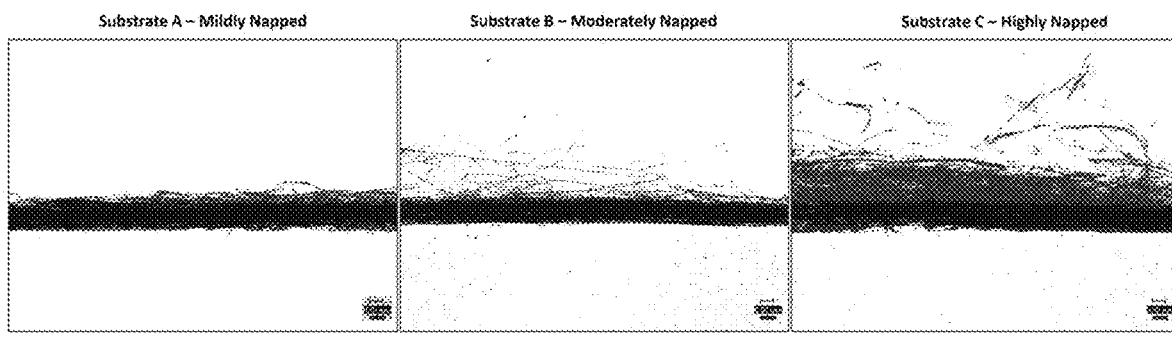
FIG. 2 illustrates a comparison of non-napped & different degrees of napped as cross-sectional images of substrates.

The most preferred process of moderately napping the surface increases the cross-sectional area by 152% (FIG. 2, Table 2). In all cases, density changes are minimal.

TABLE 2

| Condition | Non-napped area (px$^2$) | Post-napped area (px$^2$) | Matrix Area Δ (%) |
|---|---|---|---|
| Substrate A, Mildly Napped | 26.17 | 41.15 | 57.24 |
| Substrate B, Moderately Napped | 26.91 | 67.88 | 152.25 |
| Substrate C, Highly Napped | 24.31 | 129.86 | 434.18 |

Quantitative analysis of the preferred substrates demonstrated that moderate napping increased the matrix height, surface roughness and volume by 642%, 672% and 8999%, respectively (Table 3).

TABLE 3

| Napping | Maximum Height (um) | Surface Roughness, Sa (um) | Volume (μm^3) |
|---|---|---|---|
| None | 1006 | 108 | 4.4E09 |
| Mild | 4635 | 759 | 2.7E11 |
| Moderate | 7503 | 835 | 4.0E11 |
| High | 10465 | 1405 | 5.5E11 |
| None VS Mild (% Δ) | 361 | 602 | 5992 |
| None VS Moderate (% Δ) | 646 | 672 | 8999 |
| None VS High (% Δ) | 940 | 1198 | 12465 |

Figure 3:
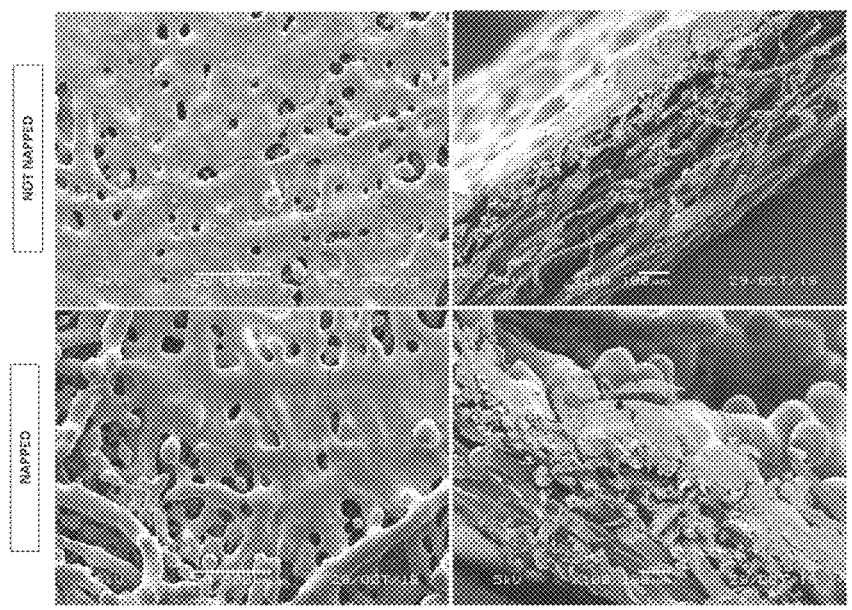
FIG. 3 illustrates aerial (left) and cross-sectional (right) SEM images of equally coated non-napped (top) and napped (bottom) substrates.

Coating the matrix without napping resulted in poor penetration and aggregation or clumping of material, whereas napping displayed improved coating of individual fibers and better penetration into the matrix. Cross-sectional SEM microscopy revealed napping alleviated the issue of "flat films" where coating caked at the surface, blocking the benefits of porous structure and increasing stiffness (FIG. 3).

Additionally, more cracks were observed in the non-napped coating. Image analysis confirmed the non-napped group only had a small number of pores and void space at the surface accounting for 12% of the total surface area, whereas the napped group had an area of 27%.

Figure 4:
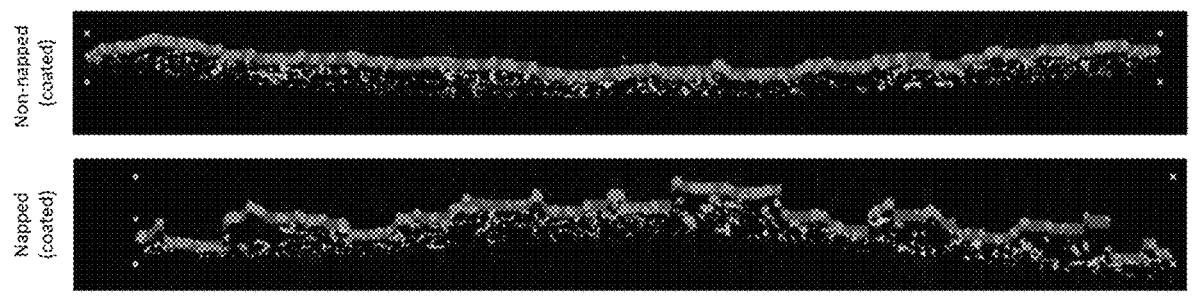
FIG. 4 illustrates images of equally coated non-napped (top) and napped (bottom) substrates via micro-CT.

Coating of individual fibers and less clumping in napped substrates illustrated improved pore volume and void space (15%) that will be beneficial for blood percolation and enhanced interlocking of coated fibers to tissue. To further corroborate these matrix characteristics, micro-CT imaging was conducted to understand the coating on napped surfaces. The visualizations reaffirmed not only how napping improved the matrix loft, but also resulted in improved penetration of the coating and increased porosity at the surface. Cross-sectional analysis showed napping disrupted the even film-like coating seen in non-napped conditions and dispersed the cross-linkers effectively without blocking the microporous structure of the matrix substrate (FIG. 4). Lastly, porosity was improved and stiffness was reduced by 13.8% and 50%, respectively (Table 4).

TABLE 4

| Sample Name | Total Porosity (%) | Mean Stiffness (N/mm) |
| --- | --- | --- |
| Non-napped, coated | 41.4 | 0.02 |
| Napped, coated | 55.2 | 0.01 |

Functional assessments were performed using a tissue peel test and a heparinized, spleen ex vivo bleeding model. For the qualified peel test the patch was applied to a calf dermal tissue and compressed in Tris Buffer Saline before peeling and measuring force at 90°.

For the ex vivo evaluation of efficacy in hemostasis, the napped, coated, non-napped coated and non-napped, uncoated, each as non-woven substrate, were assessed for reduction of bleeding. Briefly, each patch was cut into 1"×1" squares placed over a 10 mm circular biopsy defect in an ex-vivo spleen model (perfused with heparinized bovine blood) for 2 minutes with tamponade. Quantitative analysis confirmed bleeding in the ex-vivo model was minimized or entirely arrested with the use of the coated, napped melt-blown patch.

These data confirmed the hemostatic patch was fully functional and efficacious, in addition to improved tissue adhesion. Different degrees of napping influenced effectiveness of hemostat. While all patches did reduce bleeding and eventually seal to arrest, mild or high degree of napping, as described previously, had reduced effectiveness compared to moderate napping.

In one embodiment, a highly-adhesive hemostatic patch comprised of a napped melt-blown matrix substrate in combination with a cross-linkable coating can be prepared from melt-blown microfiber web using an absorbable and biocompatible polyester material, such as Monocryl®, with a drum speed of 0.17 m/s, preferably within a range tested of 0.09-0.34 m/s, and a collector distance of 25 inches, preferably within a range of 12-25 inches. Four layers can be built directly on the collector drum, with a preferred range of 2-10 layers. The resulting density of the four-layer construct is approximately 13 mg/cm$^2$ when using IV equal to 1.6 Monocryl®. These material characteristics and density are required prior to napping.

A preferred degree of napping is achieved by abrasive techniques that loosen fiber entanglement, raise surface fibers and the overall matrix height by approximately 161%, with a preferred range of 55-253%, while the cross-sectional area is subsequently increased by approximately 152%, with a preferred range of 57-434%. The resultant substrate can have increased surface roughness and volume of approximately 676% and 8999%, respectively.

Napping methods include both manual and automatic tools. Manual napping can be achieved by, and is not limited to, a wire brush, steel file cards, glass or similar tools/materials with rough edges that can be used to create abrasion. To achieve the preferred degree of napping, a steel file card (3.75") is used to brush the surface of the nonwoven fabric unidirectionally several times until fibers begin to tear off surface (5-15 times is preferred working range for this method with 5 resulting in "mild" napping and 15 resulting in "high napping"). Alternatively, automatic napping methods include and are not limited to a bench-top drill press that is used with a crimped wire wheel (e.g. 0.25" stem, 3" diameter) or other brush-based attachments. Other power-instruments and attachments such as wire brushes and abrasive flap wheels can also be utilized the achieve different degrees of napping.

In order to achieve higher degrees of napping without destructive abrasion, matrices can be subjected to heat to soften the fibers prior to brushing. The degree of heating can vary depending on polymer; for Monocryl®, the construct is heated to 50° C. for 15 minutes prior to napping.

Cross-linkable actives such as polyethylene glycol active esters (e.g. PEG-succinimidyl glutarate) are preferably coated in sequence with or without buffers and additives to develop the fully functional hemostat. To reduce the idea to practice, a 2-inch by 4-inch melt-blown matrix post-napping is either ultrasonically spray-coated (solubilized method) or dip-coated (insoluble method) with a light-layer of buffer that embeds deep into the porous substrate: working examples include a 1.25 mg/cm$^2$ of sodium borate, or 2 mg/cm$^2$ Bis-Tris or 1 mg/cm$^2$ of sodium bicarbonate. Then, 15 mg/cm$^2$ of 4arm-PEG-Amine-HCl (MW:10 Kda) is ultrasonically coated, followed by 18 mg/cm$^2$ of 4arm-PEG-SG (MW:10 Kda). The napped construct allows for unique deposition of the cross-linkable actives that results in enhanced tissue adhesion.

Exemplary plasma derived (or related) hemostatic agents include proteins and peptides, and thus are not limited, to natural and can be in recombinant or synthetic forms; prothrombin, thrombin, fibrin, fibronectin, Factor (Factor) X/Xa, Factor VII/VIIa, Factor IX/IXa, factor XI/XIa, Factor XII/XIIa, tissue factor, von Willebrand factor, elastin, albumin, platelet surface glycoproteins, vasopressin and vasopressin group consisting of analogs, epinephrine, selectin, plasminogen activator inhibitor, platelet activating agents, synthetic peptides, and any combinations thereof having hemostatic activity.

The carrier sublayers can be in the form of non-woven materials. Exemplary materials of construction are synthetic polymers. The substrate may be comprised of components selected from aliphatic polyester polymers and/or copolymers of one or more monomers selected from the group consisting of D-lactic acid, L-lactic acid, lactide (including L-, D-, meso forms), glycolic acid, glycolide, caprolactone, p-dioxanone and trimethylene carbonate and mixtures or blends thereof.

The substrate may alternatively, or additionally, be comprised of layers of fabric of aliphatic polyester polymers, copolymers, or blends thereof. The aliphatic polyesters are typically synthesized in a ring opening polymerization of monomers including, but not limited to, lactide (including L-, and D-, meso forms), glycolic acid, glycolide, caprolactone, p-dioxanone (1,4-dioxan-2-one), and trimethylene carbonate (1,3-dioxan-2-one). The aliphatic polyesters, in some cases, can be made by polycondensation of for instance, D-lactic acid, L-lactic acid and/or glycolic acid. In one form, the fabric comprises a copolymer of glycolide and lactide, in an amount ranging from about 70 to 95% by molar basis of glycolide and the remainder lactide.

The porous substrate of the dressing has openings or pores over at least a portion of a surface thereof. As described in more detail below, suitable materials for forming the porous substrate include, but are not limited to fibrous structures. In embodiments, the pores may be in sufficient number and size so as to interconnect across the entire thickness of the porous substrate.

One or more sublayers of the porous substrate can be at least 0.1 cm thick, in certain embodiments from about 0.2 to about 1.5 cm thick. The size of the pores in the sublayers of the porous substrate can be from about 2 micrometers to about 300 micrometers, in embodiments from about 50 micrometers to about 150 micrometers. It is envisioned that the pores of the sublayers of the substrate may be arranged in any manner in the substrate. For example, the pores may be configured in a random or uniform manner. In some embodiments, the pores may be formed with the use of calcium or copper alginate to create a honey-comb shaped porous substrate. In still other embodiments, the pores may be configured to create a gradient in the porous substrate. The gradient may further enhance the porous substrates ability to absorb the physiologic fluid and direct the migration of the physiological fluid carrying the first co-reactive component towards the second co-reactive component.

In one embodiment, the substrate has a first co-reactive component applied onto a first sublayer and a second co-reactive component applied thereto. The terms "first co-reactive component" and "second co-reactive component" each means a polymer, functional polymer, macromolecule, small molecule, or cross-linker that can take part in a reaction to form a network of cross-linked molecules, such as, a hydrogel.

In one embodiment, each of the first and second co-reactive components is multifunctional, meaning that it comprises two or more electrophilic or nucleophilic functional groups, such that, for example, a nucleophilic functional group on the first co-reactive component may react with an electrophilic functional group on the second co-reactive component to form a covalent bond. At least one of the first or second co-reactive components includes more than two functional groups, so that, as a result of electrophilic-nucleophilic reactions, the precursors combine to form cross-linked polymeric products. Such reactions are referred to as "cross-linking reactions".

In certain embodiments, each of the first and second co-reactive components includes only one category of functional groups, either only nucleophilic groups or only electrophilic functional groups, so long as both nucleophilic and electrophilic precursors are used in the cross-linking reaction. Thus, for example, if the first co-reactive component has nucleophilic functional groups such as amines, the second co-reactive component may have electrophilic functional groups such as N-hydroxysuccinimides. On the other hand, if first co-reactive component has electrophilic functional groups such as sulfosuccinimides, then the second co-reactive component may have nucleophilic functional groups such as amines or thiols. Thus, functional polymers such as proteins, poly(allyl amine), styrene sulfonic acid, or amine-terminated di- or multifunctional poly(ethylene glycol) ("PEG") can be used.

The first and second co-reactive components may have biologically inert and water soluble cores. When the core is a polymeric region that is water soluble, preferred polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxymethylcellulose, hyaluronic acid; and proteins such as albumin, collagen, casein, and gelatin. The polyethers and more particularly poly(oxyalkylenes) or poly(ethylene glycol) or polyethylene glycol are especially useful. When the core is small molecular in nature, any of a variety of hydrophilic functionalities can be used to make the first and second co-reactive components water soluble. For example, functional groups like hydroxyl, amine, sulfonate and carboxylate, which are water soluble, maybe used to make the precursor water soluble. In addition, N-hydroxysuccinimide ("NETS") ester of subaric acid is insoluble in water, but by adding a sulfonate group to the succinimide ring, the NETS ester of subaric acid may be made water soluble, without affecting its reactivity towards amine groups.

In certain embodiments, both the first and second co-reactive components may be large molecules that are capable of cross-linking. For example, in embodiments, one of the precursors may be a multi-functional PEG having a molecular weight of from about 2,000 to about 20,000 Daltons. This multi-functional PEG, in embodiments possessing electrophilic groups, may be reacted with a collagen having a molecular weight of about 100,000 Daltons. In other embodiments, a gelatin having a molecular weight of from about 50,000 to about 100,000 Daltons may be used in place of the collagen.

In an alternative embodiment, the co-reactive components and buffering agent are provided on a patch. An exemplary sealing patch/pad comprises: PEG-NH2*HCl and PEG-NETS, a buffering salt agent, preferably as an alkaline buffer (Borax) deposited on an absorbable substrate.

If it is desired that the biocompatible cross-linked polymer resulting from the reaction of the first and second co-reactive components be biodegradable or absorbable, one or more of the first and second co-reactive components may have biodegradable linkages present between the functional groups. The biodegradable linkage optionally also may serve as the water soluble core of one or more of the precursors. In the alternative, or in addition, the functional groups of the first and second co-reactive components may be chosen such that the product of the reaction between them results in a biodegradable linkage. For each approach, biodegradable linkages may be chosen such that the resulting biodegradable biocompatible cross-linked polymer will degrade, dissolve or be absorbed in a desired period of time. Preferably, biodegradable linkages are selected that degrade under physiological conditions into non-toxic products.

The biodegradable linkage may be chelates or chemically or enzymatically hydrolyzable or absorbable. Illustrative chemically hydrolyzable biodegradable linkages include polymers, copolymers and oligomers of glycolide, d-lactide, lactide, caprolactone, dioxanone, and trimethylene carbonate. Illustrative enzymatically hydrolyzable biodegradable linkages include peptidic linkages cleavable by metalloproteinases and collagenases. Additional illustrative biodegradable linkages include polymers and copolymers of poly (hydroxy acid)s, poly(orthocarbonate)s, poly(anhydride)s, poly(lactone)s, poly(amino acid)s, poly(carbonate)s, poly (saccharide)s and poly(phosphonate)s. In embodiments, the biodegradable linkage may contain ester linkages. Some non-limiting examples include esters of succinic acid, glutaric acid, propionic acid, adipic acid, or amino acids, as well as carboxymethyl esters.

In embodiments, a multifunctional electrophilic polymer such as a multi-arm PEG functionalized with multiple NHS groups may be used as a first co-reactive component, and a multifunctional nucleophilic component such as trilysine may be used as a second co-reactive component. In other embodiments, a multifunctional electrophilic polymer such as a multi-aim PEG functionalized with multiple NHS groups may be used as a first co-reactive component, and a multifunctional nucleophilic polymer such as collagen and/or a collagen derivative may be used as a second co-reactive component. The multi-arm PEG functionalized with multiple NHS groups can for example have four, six or eight arms and have a molecular weight of from about 5,000 to about 25,000. Many other examples of suitable first and second precursors are described in U.S. Pat. Nos. 6,152,943;

6,165,201; 6,179,862; 6,514,534; 6,566,406; 6,605,294; 6,673,093; 6,703,047; 6,818,018; 7,009,034; and 7,347,850, the entire content of each of which is incorporated herein by reference.

For the patch embodiment, the co-reactive components can be deposited upon the matrix as individual layers. Alternatively, the co-reactive components can be deposited as a mixture. The ordering of layers may change, but the preferred order sealing patch or pad comprising PEG-NH2*HCl (or any other hydrohalide), PEG-NHS, and a buffering salt (such as sodium tetraborate, MES, TRIS, Bis-Tris, sodium bicarbonate), with the matrix, then a layer of buffering salt, a layer of protected PEG-amine and a layer of the PEG-NETS. Furthermore, the number of arms and molecular weight of materials may change, but 4-arm-10K-NH2*HCl and 4-arm-10K-NETS are preferred variants from an efficacy and stability standpoint. The embodiment was evaluated with different order of coating. Performance and stability are greatly impacted by the location of the deposited buffer on the matrix using the spray-coating process. When buffer was deposited below both PEGs (i.e., furthest away from the tissue when matrix is applied), the performance and stability were optimal.

The first co-reactive component may be applied to the porous substrate using any suitable method known to those skilled in the art, including, but not limited to spraying, brushing, dipping, pouring, laminating, etc. In embodiments, the first co-reactive component may be applied as a coating on the substrate in any concentration, dimension and configuration capable of forming a hemostatic dressing. In embodiments, the first co-reactive component coating may penetrate the pores of the porous substrate. In embodiments, the first co-reactive component may be applied to the porous substrate as a film that is laminated onto at least one side of the substrate.

The second co-reactive component likewise may be applied to the porous substrate using any suitable method known to those skilled in the art, including, but not limited to spraying, brushing, dipping, pouring, laminating, etc. In still other embodiments, the second co-reactive component may be applied to the porous substrate in solution followed by evaporation or lyophilization of the solvent. In embodiments, the second co-reactive component may be applied to the porous substrate as a coating on at least one side of the substrate or as a film laminated onto at least one side of the substrate.

During use, the patch dressing is oriented with the co-reactive components applied directly onto the tissue. In embodiments, the first and second portions may be distinguishable from one another by the addition of contrast dyes, surface texturing, coloring or other visual cues. Upon contact with tissue, such as, for example, injured tissue, the dressing will soak up physiological fluid and the first co-reactive hydrogel component will be dissolved by the fluid. As the fluid wicks into and migrates through the dressing, it will carry the dissolved first co-reactive component into the second co-reactive component and buffering agent. Eventually, the first and second co-reactive components will react to form a biocompatible cross-linked material, thereby assisting clot stabilization, tissue ingrowth and remodeling as the scaffold degrades. In some embodiments, the biocompatible cross-linked material produced by reaction of the first and second co-reactive components also provide the dressing with anti-adhesive properties.

The following examples are provided for illustrative purposes only and are not intended to limit the scope of the present disclosure.

Matrix and Napping Process Example:

Meltblown microfiber web is extruded onto a drum using an absorbable and biocompatible polyester material such as Monocryl® with the most-preferred drum speed of 0.17 m/s and drum distance to die of 25 inches. Four layers are built of this configuration directly on the collector drum with the resulting density of approximately 13 mg/cm$^2$ when using IV equal to 1.6 Monocryl®. These material characteristics and density are required prior to napping.

After cutting to a 2-inch by 4-inch melt-blown matrix, the nonwoven patch is gently heated to 50° C. for 15 minutes to soften the fibers and then napped by using a 4" steel file card to brush the surface unidirectionally until the overall matrix height is increased by approximately 150%.

Coating Process Example:

A 2-inch by 4-inch melt-blown napped matrix is either ultrasonically spray-coated (solubilized method) or dip-coated (insoluble method) with a light-layer of buffer that embeds deep into the porous substrate. Working examples include a 1.25 mg/cm$^2$ of sodium borate, 2 mg/cm$^2$ Bis-Tris or 1 mg/cm$^2$ of sodium bicarbonate. Then, 15 mg/cm$^2$ of 4-arm-PEG-Amine-HCl (MW:10 Kda) is ultrasonically coated, followed by 18 mg/cm$^2$ of 4arm-PEG-SG (MW:10 Kda).

The napped construct allows for unique deposition of the cross-linkable actives, deep into the matrix, that ultimately results in a highly effective hemostat with enhanced adhesion.

We claim:

1. An absorbable tissue adhesive wound dressing comprising a melt-blown porous matrix substrate comprising a plurality of absorbable bonded melt-blown sheets having a tissue-facing surface that is napped at the surface for high tissue adhesion and coated with a coating layer that is oriented to be applied directly onto a tissue, said layer comprising co-reactive hydrogel-forming materials, applied sequentially or as a mixture, wherein (i) napping of the tissue-facing surface disrupts the coating layer relative to non-napped conditions, prevents blocking the microporous structure of the matrix substrate, and improves coating of individual fibers and better penetration into the matrix substrate, (ii) upon contact with bodily fluids, the fluids wick into and migrate through the matrix substrate, (iii) the wound dressing comprises a highly-adhesive hemostatic patch comprised of the napped melt-blown matrix substrate in combination with a cross-linkable coating that results in enhanced tissue adhesion, (iv) the napped surface results in both higher amount of coated fibers and greater surface roughness, that together enhance adhesion at the patch-tissue interface with structural integration of the hemostatic patch with tissue for enhanced adhesion, and (v) a first hydrogel-forming material is having two or more nucleophilic functional groups that react with an electrophilic functional group on a second hydrogel-forming material to form a covalent bond upon contact with the tissue.

2. A wound dressing according to claim 1, wherein the wound dressing, prior to napping, has an original thickness in the range of about 0.30-1.5 mm and an increase in a matrix height after napping prior to coating in the range of approximately 50-250% relative to the original thickness.

3. A wound dressing according to claim 1, wherein the wound dressing, prior to napping, has an original thickness in the range of about 0.6-0.95 mm, and an increase in a matrix height after napping prior to coating in the range of approximately 55-175% relative to the original thickness.

4. A wound dressing according to claim 1, wherein the wound dressing, prior to napping, has an original thickness in the range of about 0.85-0.90 mm, and an increase in a matrix height after napping prior to coating in the range of approximately 125-165% relative to the original thickness.

5. A wound dressing according to claim 1 having a density before napping in the range of about 140-250 mg/cm3.

6. A wound dressing according to claim 2 having a density before napping of about 140-200 mg/cm3.

7. A wound dressing according to claim 3 having a density before napping of about 140-150 mg/cm3.

8. A wound dressing according to claim 1 wherein the melt-blown substrate is a bioabsorbable polymeric material selected from the group consisting of polyglycolic acid (PGA), poly(lactic-co-glycolic acid) (PLGA), polylactic acid (PLA), polydioxanone (PDS), caprolactone/glycolide polyesters, poly(caprolactone-co-glycolide), and combinations thereof.

9. A wound dressing according to claim 1, wherein the melt-blown substrate is a copolymer of glycolide and epsilon-caprolactone.

* * * * *